United States Patent
Flohr et al.

(10) Patent No.: US 6,596,718 B1
(45) Date of Patent: Jul. 22, 2003

(54) 7-MORPHOLIN-4YL-BENZOTHIAZOLE AMIDE DERIVATIVES

(75) Inventors: Alexander Flohr, Basle (CH); Roland Jakob-Roetne, Inzlingen (DE); Norcross David Roger, Rheinfelden (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/298,347

(22) Filed: Nov. 18, 2002

(30) Foreign Application Priority Data

Nov. 27, 2001 (EP) .............................. 01127442

(51) Int. Cl.[7] ..................... A61K 31/5377; A61P 25/28; C07D 413/02; C07D 413/14
(52) U.S. Cl. .................... 514/233.8; 544/128; 544/131; 544/134; 544/135
(58) Field of Search .............................. 544/135, 131, 544/134, 233.8

(56) References Cited

FOREIGN PATENT DOCUMENTS

WO    WO 01/97786    12/2001

OTHER PUBLICATIONS

Poulsen et al., *Bioorganic & Med. Chem.*, vol. 6, pp. 619–641 (1998).
Muller et al., *Bioorganic & Med. Chem.*, vol. 6, pp. 707–719 (1998).
Kim et al., *J. Med. Chem.*, vol. 41, pp. 2835–2845 (1998).
Li et al., *J. Med. Chem.*, vol. 41, pp. 3186–3201 (1998).
Baraldi et al., *J. Med. Chem.*, vol. 41, pp. 2126–2133 (1998).
Li et al., *J. Med. Chem.*, vol. 42, pp. 706–721 (1999).
Baraldi et al., *J. Med. Chem.*, vol. 39, pp. 1164–1171 (1996).
Colotta et al., *Arch. Pharm. Med. Chem.*, vol. 332, pp. 39–41 (1999).
Domoki et al., *Am. J. Physiol.*, vol. 276, pp. H1113–H1116 (1999).
Haas et al., *Naunyn Schniedeberg's Arch. Pharmacol.*, vol. 362, pp. 375–381 (2000).
Dionisotti et al., *Br. J. Pharmacol.*, vol. 121, pp. 353–360 (1997).

*Primary Examiner*—Robert W Ramsuer
(74) *Attorney, Agent, or Firm*—George W. Johnston; Patricia S. Rocha-Tramaloni; Kimberly J. Prior

(57) ABSTRACT

A compound of the formula

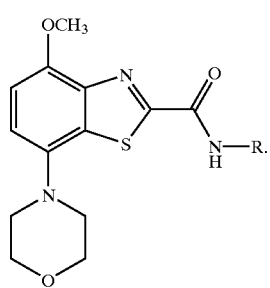

A compound of formula I has a good affinity to the $A_{2A}$ receptor and is useful for the treatment of diseases mediated by this receptor.

16 Claims, No Drawings

7-MORPHOLIN-4YL-BENZOTHIAZOLE AMIDE DERIVATIVES

FIELD OF INVENTION

The present invention is directed to a compound of the formula

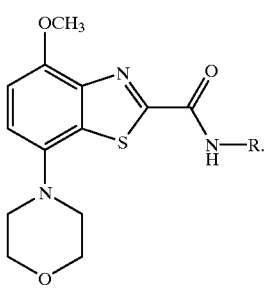

Compounds of formula I are adenosine receptor ligands. The compounds of the present invention have a good affinity to the $A_{2A}$-receptor and a high selectivity to the $A_1$- and $A_3$ receptors and as such, are useful in a method of treatment, control or prevention of illnesses based on the modulation of the adenosine system.

BACKGROUND

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes AND, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short-term imbalance of oxygen: One of the important functions of endogenous adenosine is preventing damage during traumas such as hypoxia, ischaemia, hypotension and seizure activity.

Furthermore, it is known that the binding of the adenosine receptor agonist to mast cells expressing the rat A3 receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho)physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers.

Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyperactivity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricular arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

The current knowledge on adenosine receptors is summarized in various documents including, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H1113–1116, (1999) or
Naunyn Schmied, Arch. Pharmacol. 362, 375–381, (2000).

SUMMARY

The present invention is directed to a compound of the formula

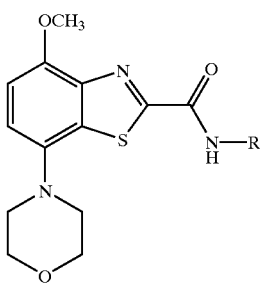

I wherein
R is selected from the group
hydrogen,
—$(CH_2)_n$-phenyl, said —$(CH_2)_n$-phenyl being unsubstituted or substituted by a substituent selected from the group halogen, lower alkyl, lower alkoxy, trifluoromethyl or —N(R')—C(O)-lower alkyl,
—$(CH_2)_n$-pyridinyl, said —$(CH_2)_n$-pyridinyl being unsubstituted or substituted by lower alkyl,
—$(CH_2)_n$—$C_{3-6}$-cycloalkyl, said —$(CH_2)_n$—$C_{3-6}$-cycloalkyl being unsubstituted or substituted by hydroxy,
—$(CH2)_n$—N(R')—$C_{3-6}$-cycloalkyl, said —$(CH_2)_n$—N(R')—$C_{3-6}$-cycloalkyl being unsubstituted or substituted by hydroxy,
—$(CH_2)_n$-benzo[1,3]-dioxolyl,
—$(CR'_2)_n$-thiophenyl, said —$(CR'_2)_n$-thiophenyl being unsubstituted or substituted by lower alkyl,
—$(CR'_2)_n$-thiazolyl, said —$(CR'_2)_n$-thiazoyl being unsubstituted or substituted by lower alkyl,
—$(CH_2)_n$—C(O)-thiophenyl, said —$(CH_2)_n$—C(O)-thiophenyl being unsubstituted or substituted by halogen,
—$(CH_2)_n$-furanyl, said —$(CH_2)_n$-furanyl being unsubstituted or substituted by lower alkyl,
—$(CH_2)_n$—C(O)—$(CH_2)_n$-thiophenyl,
—$(CHR')_n$-benzofuran-2-yl,
—$(CH_2)_n$-benzo[b]thiophenyl, said —$(CH_2)_n$-benzo[b]thiophenyl being unsubstituted or substituted by lower alkyl,
—$(CH_2)_n$—N(R')—C(O)-phenyl, said —$(CH_2)_n$—N(R')—C(O)-phenyl being unsubstituted or substituted by halogen or lower alkoxy,
—$(CH_2)_n$—C(O)-phenyl, said —$(CH_2)_n$—C(O)-phenyl being unsubstituted or substituted by lower alkoxy,
—$(CH_2)_n$—C(O)-2,3-dihydro-benzo[1,4]dioxin-6-yl,
—$(CH_2)_n$—N(R')—C(O)-pyridinyl,
—$(CH_2)_n$-tetrahydrofuranyl,
—CH-bi-phenyl,
—CH(phenyl)-pyridinyl,
—$(CH_2)_n$-1-oxo-1,3-dihydro-isoindol-2-yl,
—$(CH_2)_n$-1,3-dioxo-1,3-dihydro-isoindol-2-yl,
—$(CH_2)_n$—CH(phenyl)-tetrahydropyranyl,
—$(CH_2)_n$-1-oxo-1,2,3,4-tetrahydro-isoquinolin-3-yl and
—$(CH_2)_n$—S-[1,3,4]thiazol-2-yl, said —$(CH_2)_n$—S-[1,3,4]thiazol-2-yl being unsubstituted or substituted by amino, wherein R' is independently selected from the group consisting of hydrogen and lower alkyl; and n is 0, 1, 2, 3 or 4
or a pharmaceutically acceptable acid addition salt thereof.

It has surprisingly been found that the compounds of formula I are adenosine receptor ligands. Specifically, the compounds of the present invention have a good affinity to the $A_{2A}$-receptor and a high selectivity to the $A_1$- and $A_3$ receptors.

The present invention is directed to a compound of formula I, or a pharmaceutically acceptable salt thereof, as well as processes for the preparation of compounds of formula I. The present invention is also directed to a pharmaceutical composition comprising a therapeutically effective amount of a compound of formula I, or a pharmaceutically acceptable salt thereof, in a pharmaceutically inert carrier for the treatment of diseases related to the adenosine $A_{2A}$ receptor. The present invention also is directed to a method of control or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention maybe useful as sedatives, muscle relaxants, antipsychotics, antiepileptics, anticonvulsants and cardiaprotective agents for disorders such as coronary artery disease and heart failure comprising administering a therapeutically effective amount of a compound of formula I or a pharmaceutically acceptable salt thereof-to a person in need of such treatment.

The most preferred indications in accordance with the method of control or treatment of the present invention are those, which depend on $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present invention are compounds of formula I, wherein R is hydrogen, for example the following compound:

4-methoxy-7-morpholin-4-yl-benzothiazole-2-carboxylic acid amide.

Further preferred are compounds of formula I, wherein R is —(CH$_2$)$_n$-phenyl, said —(CH$_2$)$_n$-phenyl being unsubstituted or substituted by halogen, lower alkoxy or lower alkyl, exemplified by a compound selected from the group:

4-methoxy-7-morpholin-4-yl-benzothiazole-2-carboxylic acid phenethyl-amide, 4-methoxy-7-morpholin-4-yl-benzothiazole-2-carboxylic acid 3-chloro-benzylamide, 4-methoxy-7-morpholin-4-yl-benzothiazole-2-carboxylic acid 2-chloro-benzylamide, 4-methoxy-7-morpholin-4-yl-benzothiazole-2-carboxylic acid 2-methoxy-benzylamide, 4-methoxy-7-morpholin-4-yl-benzothiazole-2-carboxylic acid[2-(2-methoxy-phenyl)-ethyl]-amide, 4-methoxy-7-morpholin-4-yl-benzothiazole-2-carboxylic acid[2-(3-fluoro-phenyl)-ethyl]-amide, 4-methoxy-7-morpholin-4-yl-benzothiazole-2-carboxylic acid[2-(4-fluoro-phenyl)-ethyl]-amide, 4-methoxy-7-morpholin-4-yl-benzothiazole-2-carboxylic acid[2-(4-chloro-phenyl)-ethyl]-amide, 4-methoxy-7-morpholin-4-yl-benzothiazole-2-carboxylic acid[2-(2-chloro-phenyl)-ethyl]-amide, 4-methoxy-7-morpholin-4-yl-benzothiazole-2-carboxylic acid[2-(3-methoxy-phenyl)-ethyl]-amide, 4-methoxy-7-morpholin-4-yl-benzothiazole-2-carboxylic acid[2-(3-chloro-phenyl)-ethyl]-amide and 4-methoxy-7-morpholin-4-yl-benzothiazole-2-carboxylic acid (2-m-tolyl-ethyl)-amide.

Further preferred are compounds, wherein R is —(CH$_2$)$_n$-pyridinyl, said —(CH$_2$)$_n$-pyridinyl being unsubstituted or substituted by lower alkyl, selected from the group:

4-methoxy-7-morpholin-4-yl-benzothiazole-2-carboxylic acid pyridin-3-ylamide, 4-methoxy-7-morpholin-4-yl-benzothiazole-2-carboxylic acid (pyridin-2-ylmethyl)-amide and 4-methoxy-7-morpholin-4-yl-benzothiazole-2-carboxylic acid (2-pyridin-3-yl-ethyl)-amide.

Further preferred are compounds, wherein R is —(CHR')$_n$-thiophenyl or —(CH$_2$)$_n$—C(O)-thiophenyl, said thiophenyl being unsubstituted or substituted by halogen as exemplified by a compound selected from the group:

4-methoxy-7-morpholin-4-yl-benzothiazole-2-carboxylic acid (2-thiophen-2-yl-ethyl)-amide, 4-methoxy-7-morpholin-4-yl-benzothiazole-2-carboxylic acid (2-thiophen-3-yl-ethyl)-amide, 4-methoxy-7-morpholin-4-yl-benzothiazole-2-carboxylic acid[2-(3-chloro-thiophen-2-yl)-2-oxo-ethyl]-amide and 4-methoxy-7-morpholin-4-yl-benzothiazole-2-carboxylic acid (1-methyl-2-thiophen-2-yl-ethyl)-amide.

Another preferred compound is wherein R is —(CHR')$_n$-thiazolyl, said thiazolyl being unsubstituted or substituted by lower alkyl, as exemplified by:

4-methoxy-7-morpholin-4-yl-benzothiazole-2-carboxylic acid[1-(4-methyl-thiazol-2-yl)-ethyl]-amide.

The present compounds of formula I and their pharmaceutically acceptable salts can be prepared by methods known in the art, for example, by processes described below, which processes comprise a) reacting a compound of formula (5)

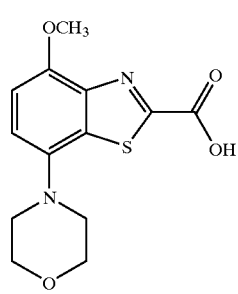

with a compound of formula

H$_2$NR  (6)

forming a compound of formula

I

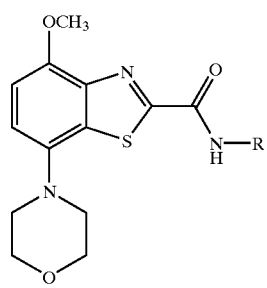

wherein R is as defined above, or b) cyclizing a compound of formula

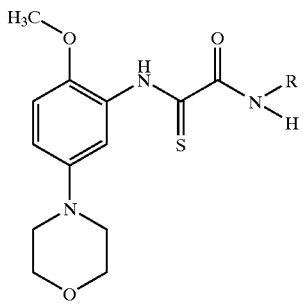

forming a compound of formula

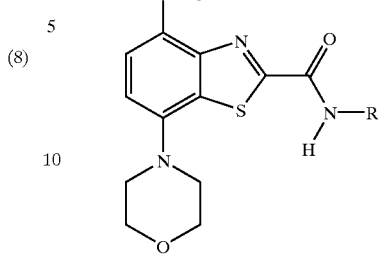

I wherein R is as described above, and
if desired, converting the compounds obtained into pharmaceutically acceptable acid addition salts.

The compounds of formula I may be prepared in accordance with process variants
a) and b) and with the following schemes 1 and 2. The preparation of 84 Examples is further described in more detail.

Scheme 1

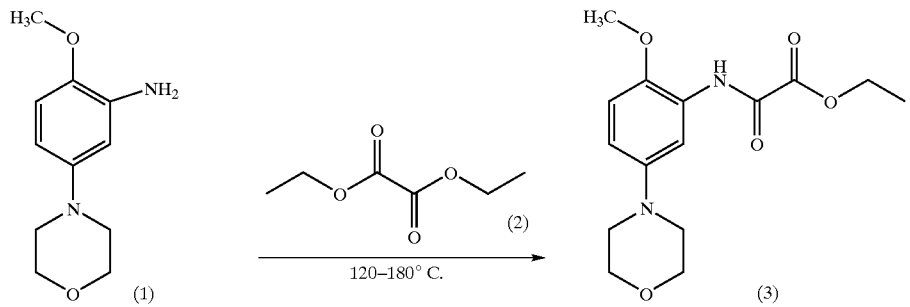

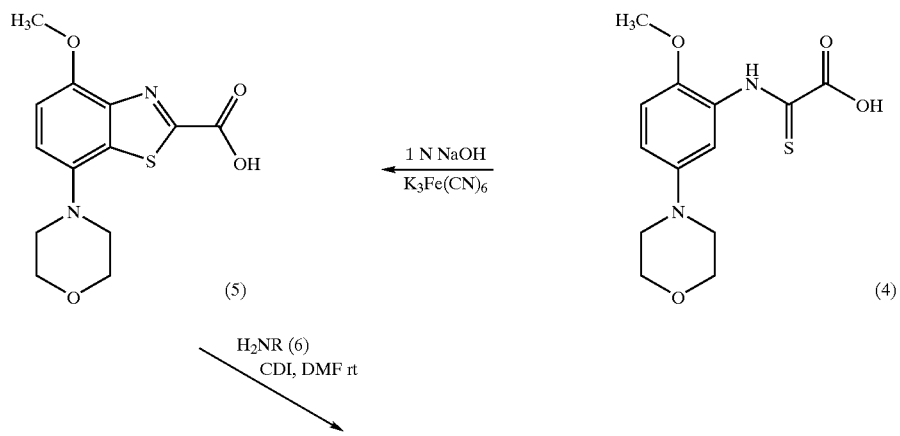

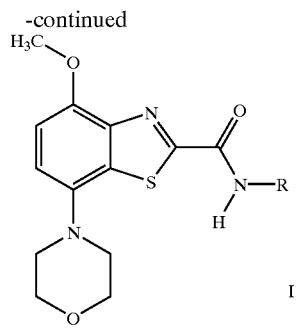

I wherein R is as described above and CDI is 1.1'-carbonyl-diimidazole.

b) The preparation of the starting compound of formula (I) has been described in WO 01/97786.

In accordance with scheme 1, the compounds of formula I are prepared as follows: Diethyl oxalate (2) is heated to about 120° C. 2-Methoxy-5-morpholin-4-yl-phenylamine (1) is added very cautiously in small quantities and the mixture is heated for 90 minutes at about 180° C. After cooling to room temperature and filtration n-hexane is added. The resulting precipitate is collected by filtration. After washing with hexane and drying N-(2-methoxy-5-morpholin-4-yl-phenyl)-oxalamic acid ethyl ester (3) is obtained. Then, to the obtained compound of formula (3) in boiling xylene is added phosphorus pentasulfide in small portions over a period of about 30 minutes. The mixture is refluxed for about 5 hours, cooled to room temperature and filtered. The solution is extracted with 1N NaOH. The aqueous phase is washed with toluene, filtered, and treated at 0–5° C. with concentrated hydrochloric acid until pH 1 was reached. Filtration of the precipitate yielded (2-methoxy-5-morpholin-4-yl-phenylamino)-thioxo-acetic acid (4).

A solution of (2-methoxy-5-morpholin-4-yl-phenylamino)-thioxo-acetic acid (4) in 1N NaOH is added to a solution of potassium ferricyanide in water at a rate that the temperature does not exceed 10° C. The mixture is stirred for 3 hours at 10° C. and concentrated hydrochloric acid is added until pH 1 was reached. Filtration of the precipitate and drying yielded 4-methoxy-7-morpholin-4-yl-benzothiazole-2-carboxylic acid (5). A suspension of the compound of formula (5) and 1.1'-carbonyl-diimidazole in dimethylformamide is stirred at room temperature for about one hour. A compound of formula (6), for example benzylamine, is added, stirring is continued and after about 20 hours water is added. After extraction with ethyl acetate and chromatography on silicagel with dichloromethane/ethyl acetate is yielded a compound of formula I.

Examples 3 to example 84 have been prepared according to scheme 1.

Scheme 2

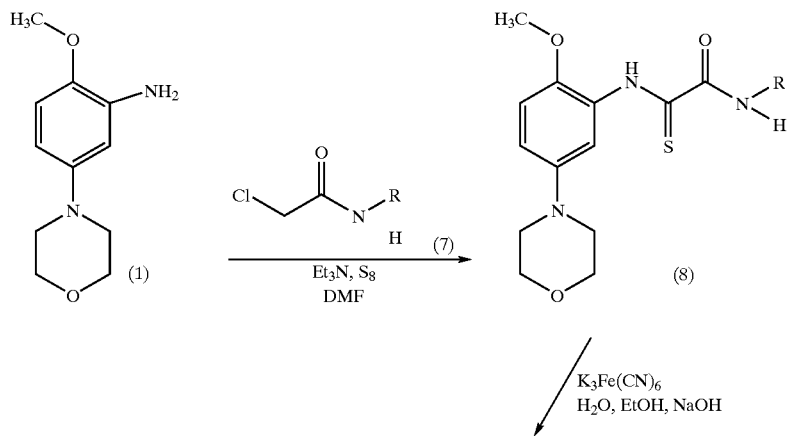

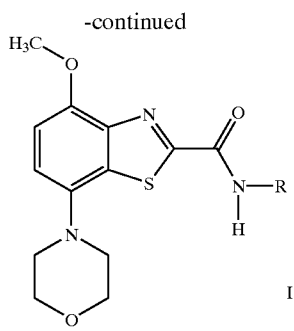

I wherein R is as defined above,

In accordance with scheme 2 the corresponding chloroacetamide of formula (7) and sulfur in dimethylformamide are treated with triethylamine, and the mixture is stirred for about 15 hours at room temperature. Then 2-methoxy-5-morpholin-4-yl-phenylamine (1) and n-propanol are added and stirring at room temperature is continued for 6 hours. The mixture is refluxed for two days. The precipitated crystals are filtered off and washed with n-propanol to yield a compound of formula (8).

A suspension of the compound of formula (8) in 1N aqueous sodium hydroxide is added to a solution of potassium ferricyanide in water. The mixture is stirred at 50° C. for about 30 minutes and then at room temperature overnight. The precipitate is separated by filtration, dissolved in dichloromethane and purified by column chromatography on silicagel with ethyl acetate/hexane to yield a compound of formula I.

Examples 1 and 2 have been prepared according to scheme 2.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of Formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, methanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of Formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor and a good selectivity towards $A_1$ and $A_3$ receptors.

The compounds were investigated in accordance with the following tests.

Human Adenosine $A_1$ Receptor

The human adenosine $A_1$ receptor was recombinantly expressed in chinese hamster ovary (CHO) cells using the semlilki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-DPCPX (([propyl-$^3$H]8-cyclopentyl-1,3-dipropyxanthine); 0.6 nM) binding assay was carried out in 96-well plates in the presence of 2.5 μg of membrane protein, 0.5 mg of Ysi-poly-l-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM–0.3 nM. All assays were conducted in duplicate and repeated at least two times. Assay plates were incubated for 1 hour at room temperature before centrifugation and then bound ligand determined using a Packard Topcount scintillation counter. $IC_{50}$, the concentration where 50% of the non-specific binding is displaced, values were calculated using a non-linear curve fitting program and $k_i$ values calculated using the Cheng-Prussoff equation.

Human Adenosine $A_{2A}$ Receptor

The human adenosine $A_{2A}$ receptor was recombinantly expressed in chinese hamster ovary (CHO) cells using the semlilki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A) The [$^3$H]-SCH-58261 (Dionisotti et al., 1997, Br J Pharmacol 121, 353; 1 nM) binding assay was carried out in 96-well plates in the presence of 2.5 μg of membrane protein, 0.5 mg of Ysipoly-l-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values, the concentration where 50% of the non-specific binding is displaced, were calculated using a non-linear curve fitting program and $K_i$ values calculated using the Cheng-Prussoff equation.

It has been shown that compounds of formula I have a good affinity to the $A_{2A}$ receptor and a high selectivity toward the $A_1$. The preferred compounds have a $pK_i$>7.5.

| Example No. | $hA_1$ ($pK_i$) | $hA_2$ ($pK_i$) |
|---|---|---|
| 1 | 5.4 | 7.6 |
| 6 | 5.9 | 7.7 |
| 9 | 5.4 | 7.8 |
| 13 | 5.2 | 7.5 |
| 15 | 5.6 | 7.7 |
| 16 | 5.4 | 7.5 |
| 22 | 5.9 | 8.4 |
| 25 | 5.1 | 7.6 |
| 49 | 5.8 | 7.5 |
| 54 | 5.9 | 8.2 |
| 55 | 5.2 | 7.6 |
| 57 | 5.8 | 7.7 |
| 59 | 5.2 | 7.5 |
| 62 | 5.7 | 7.5 |
| 63 | 6.0 | 7.7 |
| 64 | 5.9 | 7.6 |
| 65 | 6.3 | 7.6 |
| 71 | 5.9 | 7.6 |
| 73 | 5.8 | 7.5 |
| 77 | 6.3 | 8.3 |
| 81 | 6.7 | 8.9 |

The compounds of formula I and the pharmaceutically acceptable salts of the compounds of formula I can be used to prepare pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As stated above, pharmaceutical compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention a method of treatment, control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse comprises administering a therapeutically effective amount of a compound of formula I, or a pharmaceutically acceptable. Further, compounds of the present invention may be useful as sedatives, muscle relaxants, antipsychotics, antiepileptics, anticonvulsants and cardioprotective agents and for the production of corresponding pharmaceutical compositions.

The most preferred indications in accordance with the present invention include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

| | | Tablet formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

4-Methoxy-7-morpholin-4-yl-benzothiazole-2-carboxylic Acid Amide a) 2-(2-Methoxy-5-morpholin-4-yl-phenylamino)-2-thioxo-acetamide 173 mg (1.85 mmol) Chloroacetamide and 119 mg (3.70 mmol) sulfur in 2 ml dimethylformamide were treated with 772 µl (5.55 mmol) triethylamine and the mixture was stirred for 15 hours at room temperature. Then 385 mg (1.85 mmol) 2-methoxy-5-morpholin-4-yl-phenylamine and 10 ml n-propanol were added and stirring at room temperature was continued for 6 hours. The mixture was refluxed for two days. The precipitated crystals were filtered off and washed with n-propanol to yield 320 mg (59%) 2-(2-methoxy-5-morpholin-4-yl-phenylamino)-2-thioxo-acetamide as red-brown crystals. MS m/e (%): 296 (M+H$^+$, 100), MA: $C_{13}H_{17}N_3O_3S$ (295.357) calc.: C 52.87 H 5.80 N 14.23 S 10.86 found: C 52.38 H 5.82 N 13.85 S 10.86 b) 4-Methoxy-7-morpholin-4-yl-benzothiazole-2-carboxylic Acid Amide

A suspension of 220 mg (0.75 mmol) 2-(2-methoxy-5-morpholin-4-yl-phenylamino)-2-thioxo-acetamide in 2.88 ml 1N aqueous sodiumhydroxde was added to a solution of 813 mg (2.47 mmol) potassium ferricyanide in 2 ml water. The mixture was stirred at 50° C. for 30 minutes and then at room temperature overnight. The precipitate was separated by filtration, dissolved in dichloromethane and purified by column chromatography on silicagel with ethyl acetate/hexane 1/1. 4-methoxy-7-morpholin-4-yl-benzothiazole-2-carboxylic acid amide, 32 mg (15%), was obtained as yellow crystals with mp.: 228–230° C., MS m/e (%): 294 (M+H$^+$, 100).

EXAMPLE 2

4-Methoxy-7-morpholin-4-yl-benzothiazole-2-carboxylic Acid (4-Fluoro-phenyl)-amide a) N-(4-Fluoro-phenyl)-2-(2-methoxy-5-morpholin-4-yl-phenylamino)-2-thioxo-acetamide 919 mg (4.80 mmol) α-chloro-4-fluoroacetanilide and 308 mg (9.60 mmol) sulfur in 10 ml dimethylformamide were treated with 2.01 ml (14.4 mmol) triethylamine and the mixture was stirred for 2 days at room temperature. Then 1.00 g (4.80 mmol) 2-methoxy-5-morpholin-4-yl-phenylamine in 5 ml dimethylformamide and 25 ml n-propanol were added and stirring at room temperature was continued for 6 hours. The mixture was refluxed for 6.5 hours. The precipitated crystals were filtered off and washed with water and dried to yield 434 mg (24%) N-(4-fluoro-phenyl)-2-(2-methoxy-5-morpholin-4-yl-phenylamino)-2-thioxo-acetamide as red powder with mp.: 206–208° C., MS m/e (%): 390 (M+H$^+$, 100).

b) 4-Methoxy-7-morpholin-4-yl-benzothiazole-2-carboxylic Acid (4-Fluoro-phenyl)-amide A suspension of 100 mg (0.26 mmol) N-(4-fluoro-phenyl)-2-(2-methoxy-5-morpholin-4-yl-phenylamino)-2-thioxo-acetamide in 3.60 ml 1N aqueous sodium hydroxide was added to a solution of 285 mg (0.87 mmol) potassium ferricyanide in 1 ml water. The mixture was stirred at 50° C. for two days and then extracted with dichloromethane. Purification by column chromatography on silicagel with ethyl acetate/hexane 3/7 yielded 3.5 m;, 4-methoxy-7-morpholin-4-yl-benzothiazole-2-carboxylic acid (4-fluoro-phenyl)-amide as off-white crystals, MS m/e (%): 388 (M+H$^+$, 100)

EXAMPLE 3

4-Methoxy-7-morpholin-4-yl-benzothiazole-2-carboxylic Acid Benzylamide a) N-(2-Methoxy-5-morpholin-4-yl-phenyl)-oxalamic Acid Ethyl Ester 139 ml (1015 mmol) Diethyl oxalate were heated to 120° C. 30.3 g (145 mmol) 2-methoxy-5-morpholin-4-yl-phenylamine were added very cautiously in small quantities and the mixture was heated for 90 minutes at 180° C. After cooling to room temperature and filtration 1.5 l n-hexane were added. The resulting precipitate was collected by filtration. After washing with hexane and drying 34.4 g (77%) N-(2-methoxy-5-morpholin-4-yl-phenyl)-oxalamic acid ethyl ester was obtained as greenish crystals, mp.: 95–97° C., MS m/e (%): 309 (M+H$^+$, 100).

b) (2-Methoxy-5-morpholin-4-yl-phenylamino)-thioxo-acetic Acid

To 33.9g (110 mmol) N-(2-methoxy-5-morpholin-4-yl-phenyl)-oxalamic acid ethyl ester in 652 ml boiling xylene were added 8.80 g (40 mmol) phosphorus pentasulfide in small portions over a period of 30 minutes. The mixture was refluxed for 5 hours, cooled to room temperature and filtered. The solution was extracted 7 times with 100 ml 1N NaOH. The aqueous phase was washed twice with 100 ml toluene, filtered, and treated at 0–5° C. with concentrated hydrochloric acid until pH 1 was reached. Filtration of the precipitate yielded 20.2 g (62%) (2-methoxy-5-morpholin-4-yl-phenylamino)-thioxo-acetic acid as yellow crystals with mp.: 156–158° C., MS m/e (%): 297 (M+H$^+$, 100).

c) 4-Methoxy-7-morpholin-4-yl-benzothiazole-2-carboxylic Acid

A solution of 10.5 g (35.4 mmol) (2-methoxy-5-morpholin-4-yl-phenylamino)-thioxo-acetic acid in 248 ml (248 mmol) 1N NaOH was added drop-wise to a solution of 40.1 g (119 mmol) potassium ferricyanide in 119 ml water at a rate that the temperature did not exceed 10° C. The mixture was stirred for 3 hours at 10° C. and concentrated hydrochloric acid was added until pH 1 was reached. Filtration of the precipitate and drying yielded 8.80 g (84%) 4-methoxy-7-morpholin-4-yl-benzothiazole-2-carboxylic acid as yellow crystals with mp.: 99–100° C., MS m/e (%): 295 (M+H$^+$, 100).

d) 4-Methoxy-7-morpholin-4-yl-benzothiazole-2-carboxylic Acid Benzylamide

A suspension of 29.4 mg (0.10 mmol) 4-methoxy-7-morpholin-4-yl-benzothiazole-2-carboxylic acid and 18.4 mg (0.11 mmol) 1.1'-carbonyl-diimidazole in 3 ml dimethylformamide was stirred at room temperature for one hour. 12.1 µl (0.11 mmol) benzylamine were added, stirring was continued and after 20 hours 15 ml water were added. Extraction with ethyl acetate and chromatography on silicagel with dichloromethane/ethyl acetate 95/5 yielded 31.2 mg (41%) of yellow 4-methoxy-7-morpholin-4-yl-benzothiazole-2-carboxylic acid benzylamide with mp.: 156–158° C., MS m/e (%): 384 (M+H$^+$, 100).

According to example 3d derivatives have been synthesized. They are compiled in the following list comprising example 4 to example 81:

| Exp. No. | Structure | Systematic name | m.p. ° C. | adduct |
|---|---|---|---|---|
| 4 | 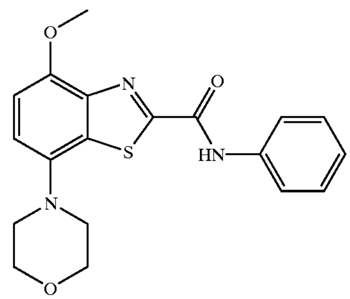 | 4-Methoxy-7-morpholin-4-yl-benzothiazole-2-carboxylic acid phenylamide | 190–191 | Aniline |
| 5 | 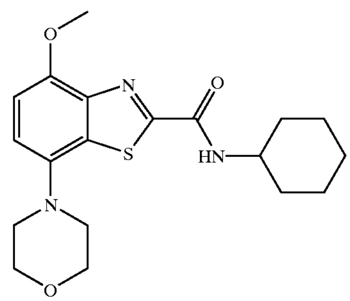 | 4-Methoxy-7-morpholin-4-yl-benzothiazole-2-carboxylic acid cyclohexylamide | 146–147 | Cyclohexylamine |
| 6 | 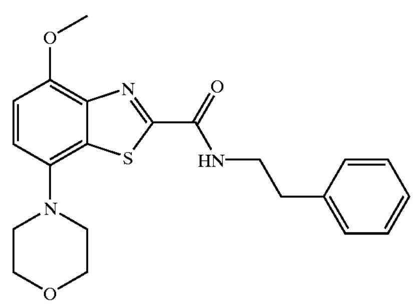 | 4-Methoxy-7-morpholin-4-yl benzothiazole-2-carboxylic acid phenethyl-amide | 50–51 | Phenylethylamine |
| 7 | 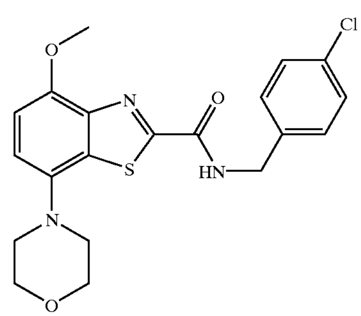 | 4-Methoxy-7-morpholin-4-yl-benzothiazole-2-carboxylic acid 4-chloro-benzylamide | 175–176 | 4-Chloro-benzylamine |
| 8 | 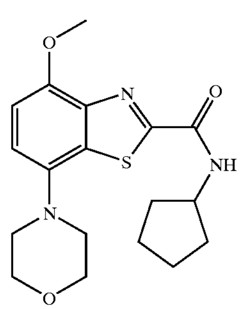 | 4-Methoxy-7-morpholin-4-yl-benzothiazole-2-carboxylic acid cyclopentylamide | 174–175 | Cyclopentyl-amine |

-continued

| Exp. No. | Structure | Systematic name | m.p. °C. | adduct |
|---|---|---|---|---|
| 9 | 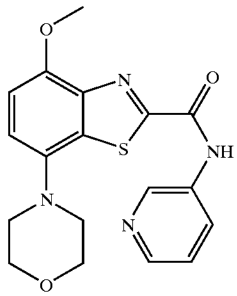 | 4-Methoxy-7-morpholin-4-yl-benzothiazole-2-carboxylic acid pyridin-3-ylamide | 220–221 | 3-Amino-pyridin |
| 10 | 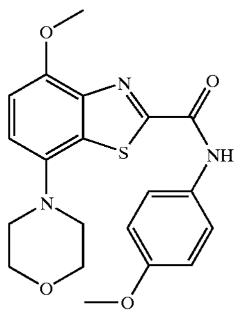 | 4-Methoxy-7-morpholin-4-yl-benzothiazole-2-carboxylic acid (4-methoxy-phenyl)-amide | 148 | p-Anisidin |
| 11 | 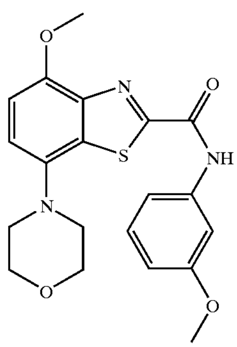 | 4-Methoxy-7-morpholin-4-yl-benzothiazole-2-carboxylic acid (3-methoxy-phenyl)-amide | 160 | m-Anisidin |
| 12 | 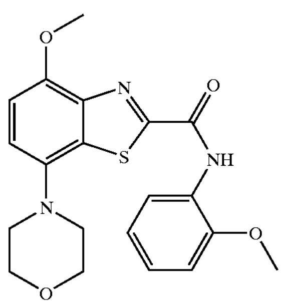 | 4-Methoxy-7-morpholin-4-yl-benzothiazole-2-carboxylic acid (2-methoxy-phenyl)-amide | 191 | o-Anisidin |
| 13 | 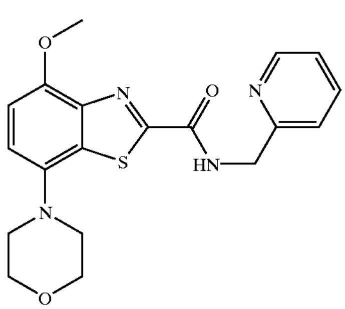 | 4-Methoxy-7-morpholin-4-yl-benzothiazole-2-carboxylic acid (pyridin-2-ylmethyl)-amide | 181–182 | 2-Amino-methyl-pyridine |

-continued

| Exp. No. | Structure | Systematic name | m.p. °C. | adduct |
|---|---|---|---|---|
| 14 | 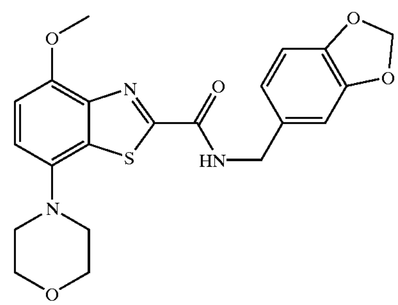 | 4-Methoxy-7-morpholin-4-yl-benzothiazole-2-carboxylic acid (benzo[1,3]dioxol-5-ylmethyl)-amide | 190–193 | 1,3-Benzo-dioxole-5-methyl-amine |
| 15 | 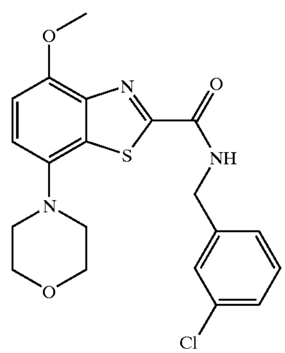 | 4-Methoxy-7-morpholin-4-yl-benzothiazole-2-carboxylic acid 3-chloro-benzylamide | 148–150 | 3-Chloro-benzylamine |
| 16 | 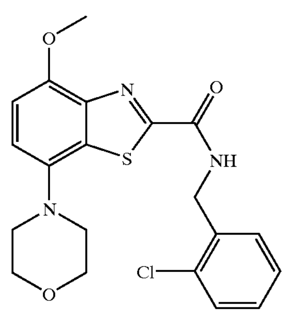 | 4-Methoxy-7-morpholin-4-yl-benzothiazole-2-carboxylic acid 2-chloro-benzylamide | 114–116 | 2-Chloro-benzylamine |
| 17 | 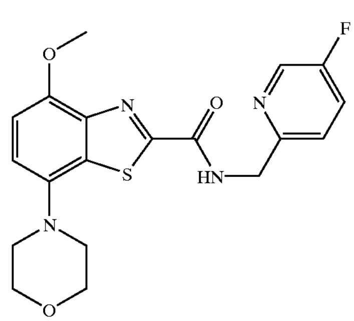 | 4-Methoxy-7-morpholin-4-yl-benzothiazole-2-carboxylic acid 4-fluoro-benzylamide | 155–156 | 4-Fluoro-benzylamine |

-continued

| Exp. No. | Structure | Systematic name | m.p. ° C. | adduct |
|---|---|---|---|---|
| 18 | 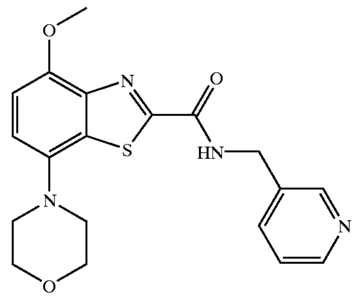 | 4-Methoxy-7-morpholin-4-yl-benzothiazole-2-carboxylic acid (pyridin-3-ylmethyl)-amide | 181–184 | 3-(Amino-methyl)-pyridine |
| 19 | 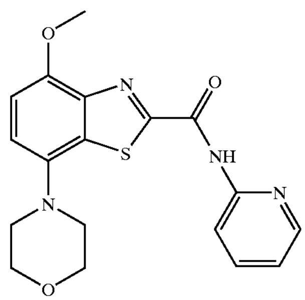 | 4-Methoxy-7-morpholin-4-yl-benzothiazole-2-carboxylic acid pyridin-2-ylamide | 177–181 | 2-Amino-pyridine |
| 20 | 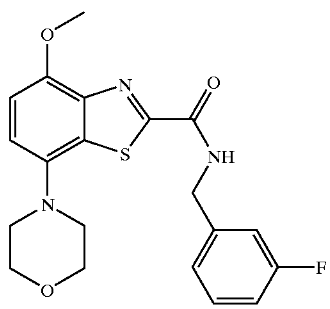 | 4-Methoxy-7-morpholin-4-yl-benzothiazole-2-carboxylic acid 3-fluoro-benzylamide | 152–153 | 3-Fluro-benzylamine |
| 21 | 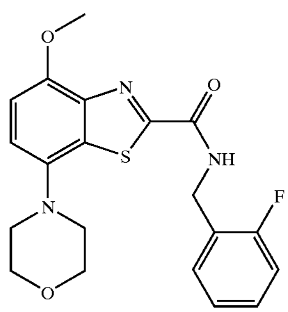 | 4-Methoxy-7-morpholin-4-yl-benzothiazole-2-carboxylic acid 2-fluoro-benzylamide | 133–134 | 2-Fluoro-benzylamine |
| 22 | 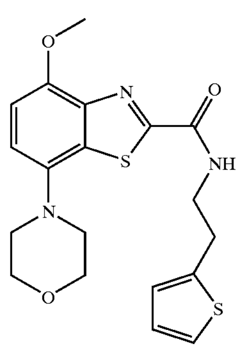 | 4-Methoxy-7-morpholin-4-yl-benzothiazole-2-carboxylic acid (2-thiophen-2-yl-ethyl)-amide | 120–121 | 2-(2-Thienyl)-ethylamine |

-continued

| Exp. No. | Structure | Systematic name | m.p. ° C. | adduct |
|---|---|---|---|---|
| 23 | 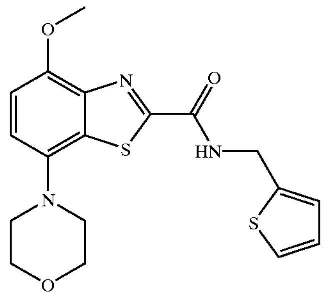 | 4-Methoxy-7-morpholin-4-yl-benzothiazole-2-carboxylic acid (thiophen-2-ylmethyl)-amide | 174–175 | 2-Thiophen-methylamine |
| 24 | 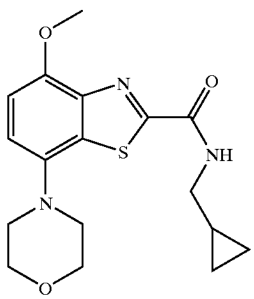 | 4-Methoxy-7-morpholin-4-yl-benzothiazole-2-carboxylic acid cyclopropylmethyl-amide | 152–153 | (Amino-methyl)-cyclopropane |
| 25 | 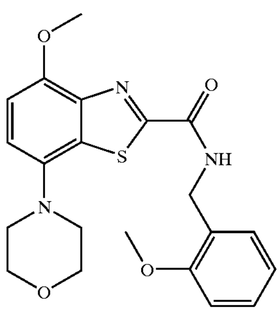 | 4-Methoxy-7-morpholin-4-yl-benzothiazole-2-carboxylic acid 2-methoxy-benzylamide | 186–188 | 2-Methoxy-benzylamine |
| 26 | 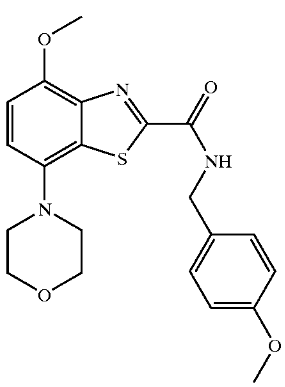 | 4-Methoxy-7-morpholin-4-yl-benzothiazole-2-carboxylic acid 4-methoxy-benzylamide | 164–168 | 4-Methoxy-benzylamine |

-continued

| Exp. No. | Structure | Systematic name | m.p. °C. | adduct |
|---|---|---|---|---|
| 27 | 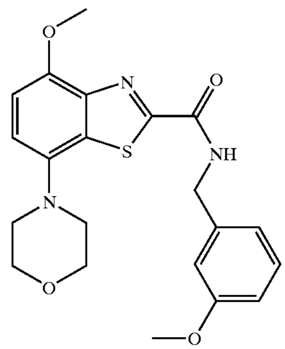 | 4-Methoxy-7-morpholin-4-yl-benzothiazole-2-carboxylic acid 3-methoxy-benzylamide | 140–144 | 3-Methoxy-benzylamine |
| 28 | 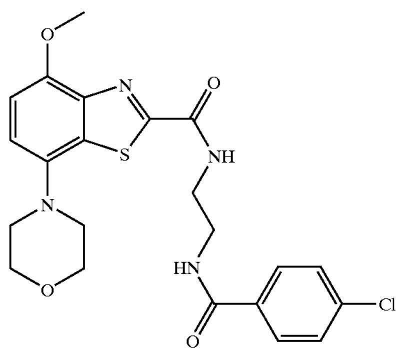 | 4-Methoxy-7-morpholin-4-yl-benzothiazole-2-carboxylic acid [2-(4-chloro-benzoylamino)-ethyl]-amide | 237–240 | N-(2-Aminoethyl)-p-chloro-benzamide |
| 29 | 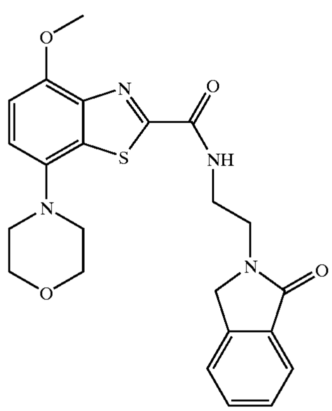 | 4-Methoxy-7-morpholin-4-yl benzothiazole-2-carboxylic acid [2-(1-oxo-1,3-dihydro-isoindol-2-yl)-ethyl]-amide | 199–205 | 2-(2-Aminoethyl)-phthal-imidine |
| 30 | 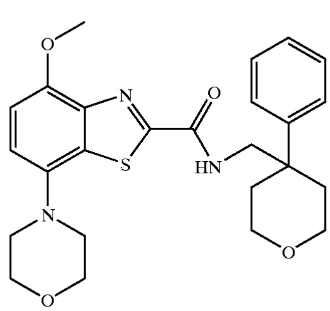 | 4-Methoxy-7-morpholin-4-yl-benzothiazole-2-carboxylic acid (4-phenyl-tetrahydro-pyran-4-ylmethyl)-amide | 144–148 | 4-Phenyl-4-methyl-amino-tetrahydro-pyran |

| Exp. No. | Structure | Systematic name | m.p. ° C. | adduct |
|---|---|---|---|---|
| 31 | 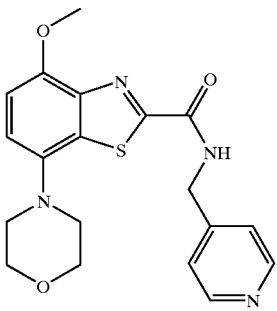 | 4-Methoxy-7-morpholin-4-yl-benzothiazole-2-carboxylic acid (pyridin-4-ylmethyl)-amide | 207–209 | 4-Picolylamine |
| 32 | 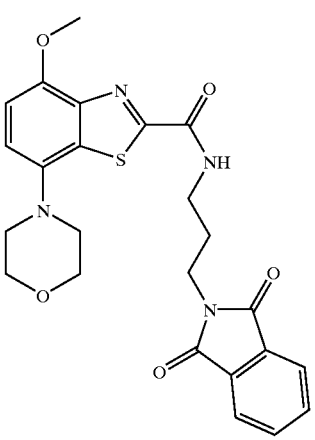 | 4-Methoxy-7-morpholin-4-yl-benzothiazole-2-carboxylic acid [3-(1,3-dioxo-1,3-dihydro-isoindol-2-yl)-propyl]-amide | 200–202 | N-(3-Amino-propyl)-phthalimide |
| 33 | 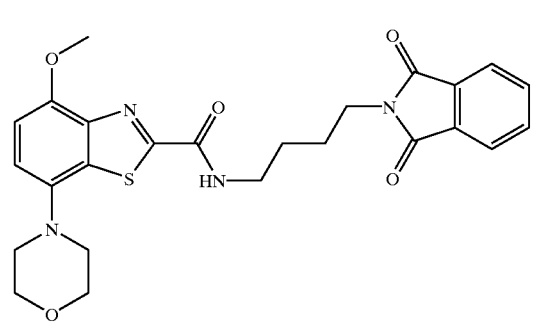 | 4-Methoxy-7-morpholin-4-yl-benzothiazole-2-carboxylic acid [4-(1,3-dioxo-1,3-dihydro-isoindol-2-yl)-butyl]-amide | 114–118 | N-(4-Amino-butyl)-phthalimide |
| 34 | 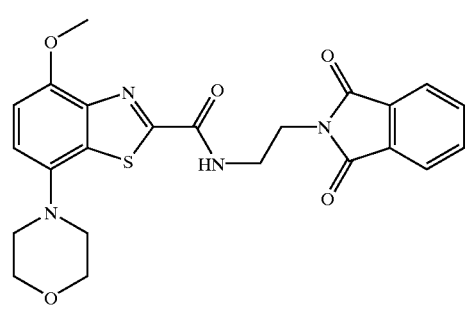 | 4-Methoxy-7-morpholin-4-yl-benzothiazole-2-carboxylic acid [2-(1,3-dioxo-1,3-dihydro-isoindol-2-yl)-ethyl]-amide | 231–233 | N-(2-Amino-ethyl)-phthalimide |

| Exp. No. | Structure | Systematic name | m.p. ° C. | adduct |
|---|---|---|---|---|
| 35 | 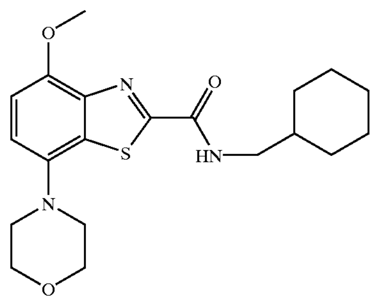 | 4-Methoxy-7-morpholin-4-yl-benzothiazole-2-carboxylic acid cyclohexylmethyl-amide | 150–151 | Cyclohexyl-methylamine |
| 36 | 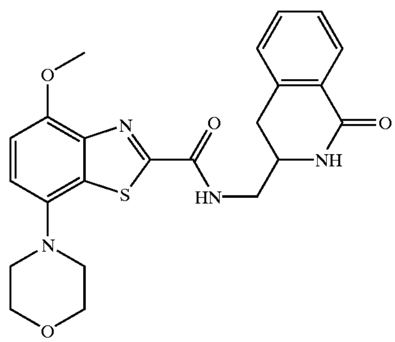 | 4-Methoxy-7-morpholin-4-yl-benzothiazole-2-carboxylic acid (1-oxo-1,2,3,4-tetrahydro-isoquinolin-3-ylmethyl)-amide | 152–155 | 3-(Amino-methyl)-3,4-dihydro-1(2H)-iso-quinolinone |
| 37 | 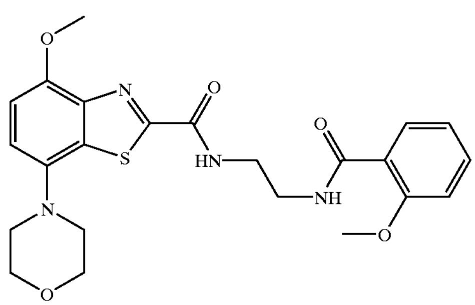 | 4-Methoxy-7-morpholin-4-yl-benzothiazole-2-carboxylic acid [2-(2-methoxy-benzoylamino)-ethyl]-amide | 180–183 | N-(2-Aminoethyl)-o-anisamide |
| 38 | 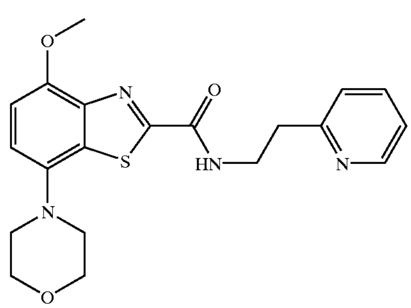 | 4-Methoxy-7-morpholin-4-yl-benzothiazole-2-carboxylic acid (2-pyridin-2-yl-ethyl)-amide | 184–185 | 2-(2-Pyridyl)-ethylamine |
| 39 | 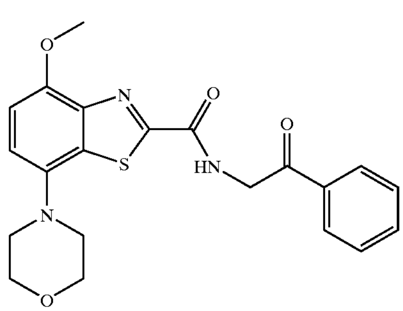 | 4-Methoxy-7-morpholin-4-yl-benzothiazole-2-carboxylic acid (2-oxo-2-phenyl-ethyl)-amide | 197–200 | Aminoaceto-phenone |

| Exp. No. | Structure | Systematic name | m.p. °C. | adduct |
|---|---|---|---|---|
| 40 | 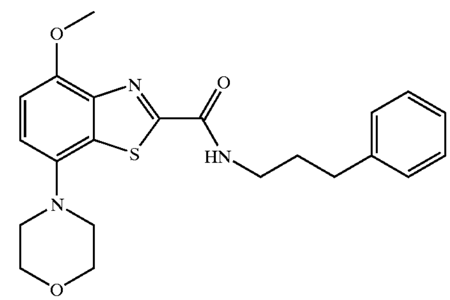 | 4-Methoxy-7-morpholin-4-yl-benzothiazole-2-carboxylic acid (3-phenyl-propyl)-amide | 147 | 3-Phenyl-propylamine |
| 41 | 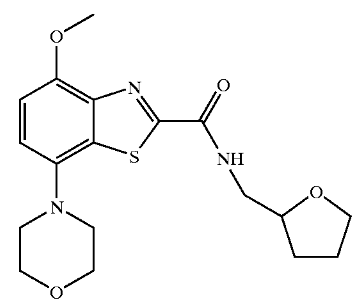 | 4-Methoxy-7-morpholin-4-yl-benzothiazole-2-carboxylic acid (tetrahydro-furan-2-ylmethyl)-amide | 171–172 | Tetrahydro-furfuryl-amine |
| 42 | 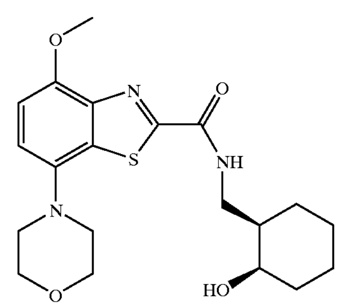 | 4-Methoxy-7-morpholin-4-yl-benzothiazole-2-carboxylic acid (2-hydroxy-cyclohexylmethyl)-amide | 178–180 | cis-2-Amino-ethyl-1-cyclohexanol |
| 43 | 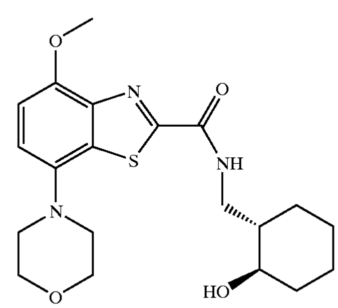 | 4-Methoxy-7-morpholin-4-yl-benzothiazole-2-carboxylic acid (2-hydroxy-cyclohexylmethyl)-amide | 133–135 | trans-2-Aminoethyl-1-cyclo-hexanol |
| 44 | 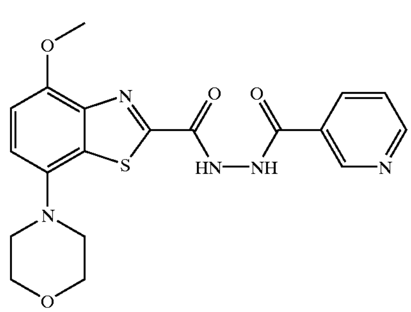 | Nicotinic acid N'-(4-methoxy-7-morpholin-4-yl-benzothiazole-2-carbonyl)-hydrazide | 222–224 | Nicotinic acid hydrazide |

-continued

| Exp. No. | Structure | Systematic name | m.p. ° C. | adduct |
|---|---|---|---|---|
| 45 | 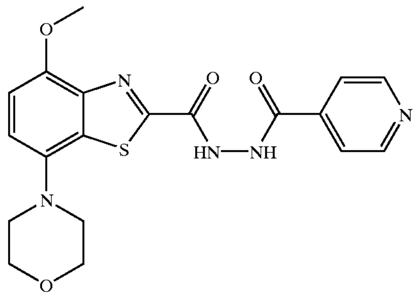 | Isonicotinic acid N'-(4-methoxy-7-morpholin-4-yl-benzothiazole-2-carbonyl)-hydrazide | 171–174 | Isonicotinic acid hydrazide |
| 46 | 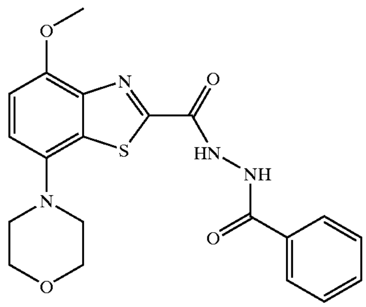 | 4-Methoxy-7-morpholin-4-yl-benzothiazole-2-carboxylic acid N'-benzoyl-hydrazide | >260° C. | Benz-hydrazide |
| 47 | 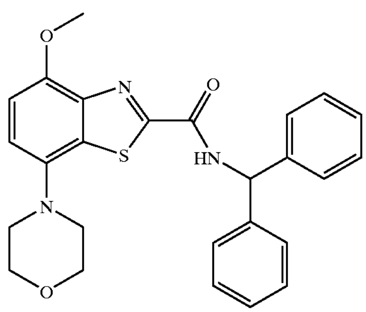 | 4-Methoxy-7-morpholin-4-yl-benzothiazole-2-carboxylic acid benzhydryl-amide | 166–168 | alpha-Amino-diphenyl-methane |
| 48 | 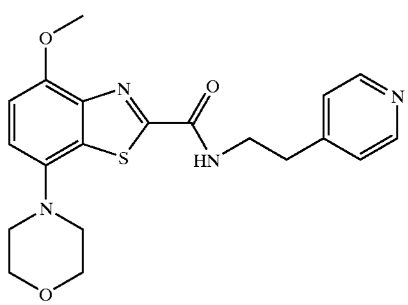 | 4-Methoxy-7-morpholin-4-yl-benzothiazole-2-carboxylic acid (2-pyridin-4-yl-ethyl)-amide | 185–188 | 4-(2-Aminoethyl)-pyridine |
| 49 | 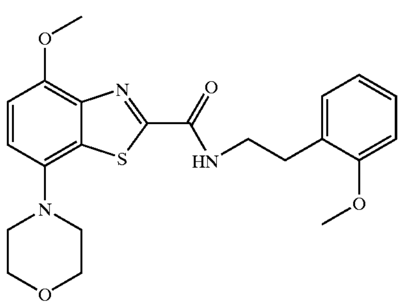 | 4-Methoxy-7-morpholin-4-yl-benzothiazole-2-carboxylic acid [2-(2-methoxy-phenyl)-ethyl]-amide | 158–160 | 2-(2-Methoxy-phenyl)-ethylamine |

-continued

| Exp. No. | Structure | Systematic name | m.p. ° C. | adduct |
|---|---|---|---|---|
| 50 | 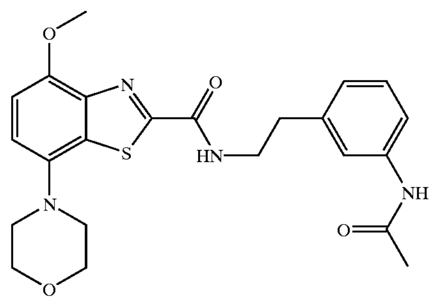 | 4-Methoxy-7-morpholin-4-yl-benzothiazole-2-carboxylic acid [2-(3-acetylamino-phenyl)-ethyl]-amide | 165–166 | 2-(3-Acetylamino-phenyl)-ethylamine |
| 51 | 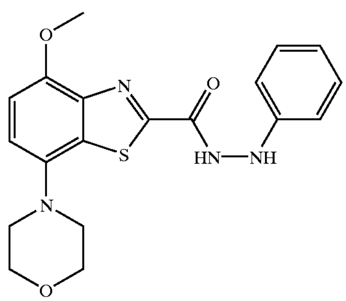 | 4-Methoxy-7-morpholin-4-yl-benzothiazole-2-carboxylic acid N'-phenyl-hydrazide | 226–227 | Phenyl-hydrazine |
| 52 | 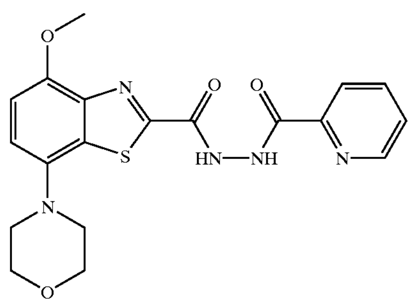 | Pyridine-2-carboxylic acid N'-(4-methoxy-7-morpholin-4-yl-benzothiazole-2-carbonyl)-hydrazide | 225–226 | 2-Picolinyl hydrazide |
| 53 | 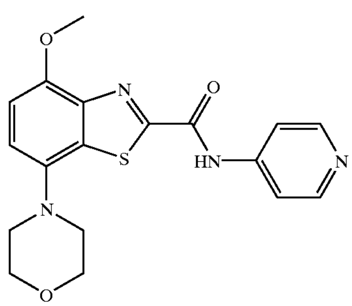 | 4-Methoxy-7-morpholin-4-yl-benzothiazole-2-carboxylic acid pyridin-4-ylamide | 206–207 | 4-Amino-pyridine |
| 54 | 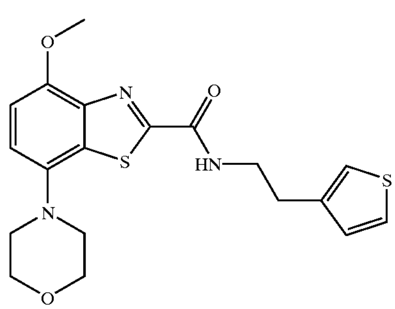 | 4-Methoxy-7-morpholin-4-yl-benzothiazole-2-carboxylic acid (2-thiophen-3-yl-ethyl)-amide | 137–139 | 3-Thiophene-ethylamine |

-continued

| Exp. No. | Structure | Systematic name | m.p. ° C. | adduct |
|---|---|---|---|---|
| 55 | 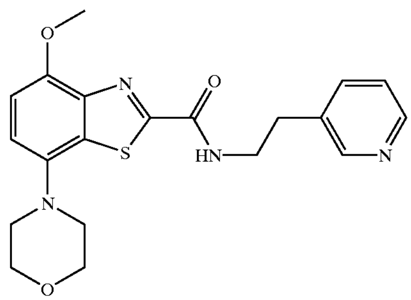 | 4-Methoxy-7-morpholin-4-yl-benzothiazole-2-carboxylic acid (2-pyridin-3-yl-ethyl)-amide | 160–163 | 3-(2-Aminoethyl)-pyridine |
| 56 | 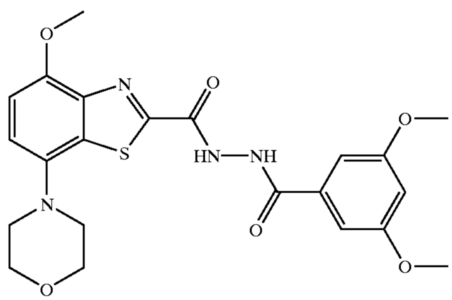 | 3,5-Dimethoxy-benzoic acid N'-(4-methoxy-7-morpholin-4-yl-benzothiazole-2-carbonyl)-hydrazide | 146–148 | 3,5-Dimethoxy-benz-hydrazide |
| 57 | 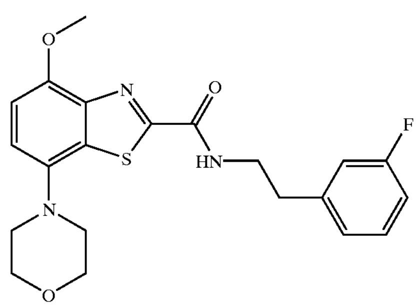 | 4-Methoxy-7-morpholin-4-yl-benzothiazole-2-carboxylic acid [2-(3-fluoro-phenyl)-ethyl]-amide | 120–122 | 3-Fluoro-phenyl-ethylamine |
| 58 | 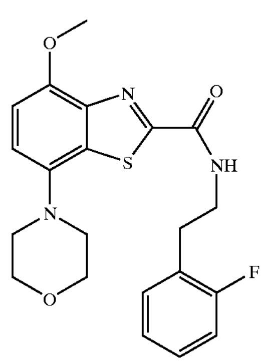 | 4-Methoxy-7-morpholin-4-yl-benzothiazole-2-carboxylic acid [2-(2-fluoro-phenyl)-ethyl]-amide | 151–153 | 2-Fluoro-phenyl-ethylamine |

-continued

| Exp. No. | Structure | Systematic name | m.p. ° C. | adduct |
|---|---|---|---|---|
| 59 | 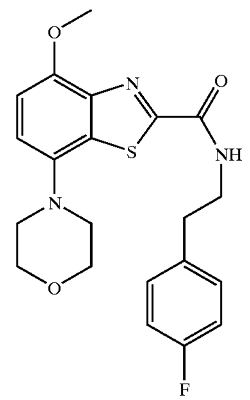 | 4-Methoxy-7-morpholin-4-yl-benzothiazole-2-carboxylic acid [2-(4-fluoro-phenyl)-ethyl]-amide | 150–153 | 4-Fluoro-phenyl-ethylamine |
| 60 | 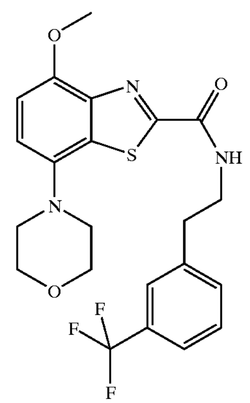 | 4-Methoxy-7-morpholin-4-yl-benzothiazole-2-carboxylic acid 2-(3-trifluoromethyl-phenyl)-ethyl]-amide | 106–108 | 2-(3-Trifluoro-methyl-phenyl)-ethylamine |
| 61 | 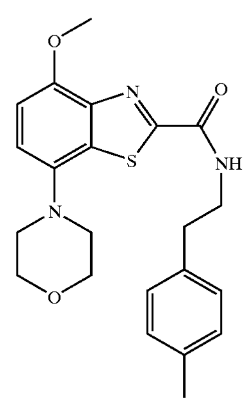 | 4-Methoxy-7-morpholin-4-yl-benzothiazole-2-carboxylic acid (2-p-tolyl-ethyl)-amide | 136–138 | 4-Methyl-phenyl-ethylamine |

-continued

| Exp. No. | Structure | Systematic name | m.p. °C. | adduct |
|---|---|---|---|---|
| 62 | 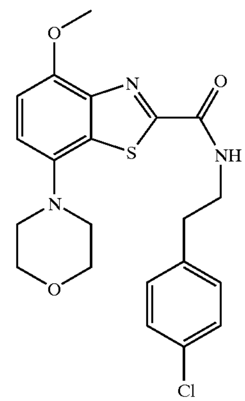 | 4-Methoxy-7-morpholin-4-yl-benzothiazole-2-carboxylic acid [2-(4-chloro-phenyl)-ethyl]-amide | 153–154 | 2-(4-Chloro-phenyl)-ethylamine |
| 63 | 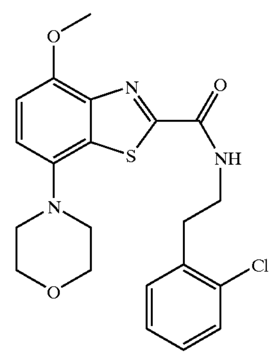 | 4-Methoxy-7-morpholin-4-yl-benzothiazole-2-carboxylic acid [2-(2-chloro-phenyl)-ethyl]-amide | 141–143 | 2-(2-Chloro-phenyl)-ethylamine |
| 64 | 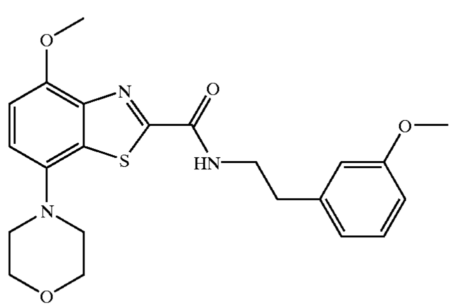 | 4-Methoxy-7-morpholin-4-yl-benzothiazole-2-carboxylic acid [2-(3-methoxy-phenyl)-ethyl] amide | 99–101 | 3-Methoxy-phenylethyl-amide |
| 65 | 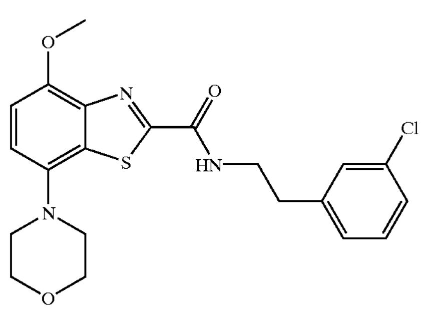 | 4-Methoxy-7-morpholin-4-yl-benzothiazole-2-carboxylic acid [2-(3-chloro-phenyl)-ethyl]-amide | 109–111 | 3-Chlorphenyl-ethylamine |

-continued

| Exp. No. | Structure | Systematic name | m.p. ° C. | adduct |
|---|---|---|---|---|
| 66 | 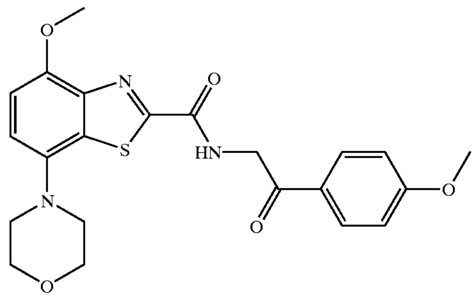 | 4-Methoxy-7-morpholin-4-yl-benzothiazole-2-carboxylic acid [2-(4-methoxy-phenyl)-2-oxo-ethyl]-amide | 176–178 | 2-amino-4'-methoxy-aceto-phenone |
| 67 | 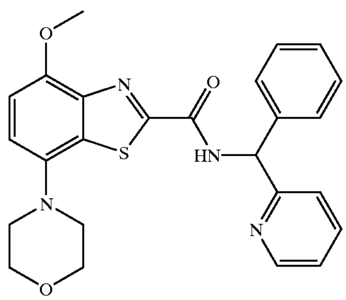 | 4-Methoxy-7-morpholin-4-yl-benzothiazole-2-carboxylic acid (phenyl-pyridin-2-yl-methyl)-amide | 219–221 | Phenyl-(2-pyridyl)-methylamine |
| 68 | 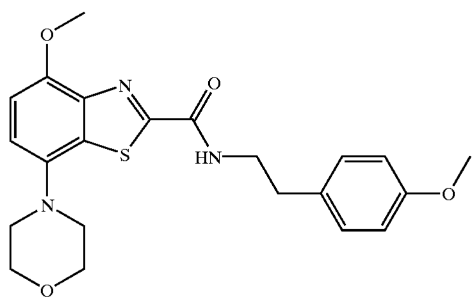 | 4-Methoxy-7-morpholin-4-yl-benzothiazole-2-carboxylic acid [2-(4-methoxy-phenyl)-ethyl]-amide | 69–71 | 4-Methoxy-phenylethyl-amine |
| 69 | 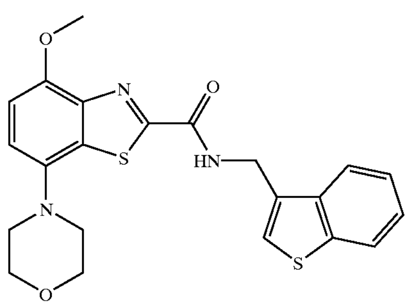 | 4-Methoxy-7-morpholin-4-yl-benzothiazole-2-carboxylic acid (benzo[b]thiophen-3-ylmethyl)-amide | 187–189 | Benzo(b)thiophen-3-yl-methylamine |
| 70 | 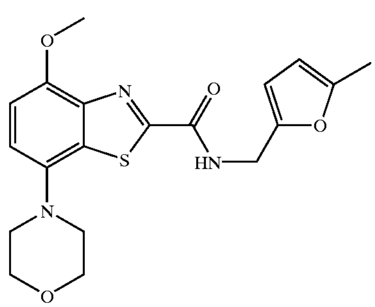 | 4-Methoxy-7-morpholin-4-yl-benzothiazole-2-carboxylic acid (5-methyl-furan-2-ylmethyl)-amide | 173–174 | 5-Methyl-furfuryl-amine |

-continued

| Exp. No. | Structure | Systematic name | m.p. °C. | adduct |
|---|---|---|---|---|
| 71 | 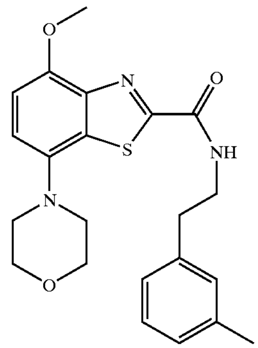 | 4-Methoxy-7-morpholin-4-yl-benzothiazole-2-carboxylic acid (2-m-tolyl-ethyl)-amide | 119–121 | 3-Methyl-phenethyl-amine |
| 72 | 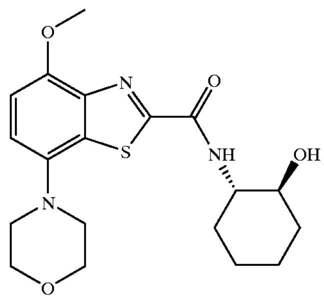 | 4-Methoxy-7-morpholin-4-yl-benzothiazole-2-carboxylic acid (2-hydroxy-cyclohexyl)-amide | 110–115 | trans-2-Amino-cyclohexanol |
| 73 | 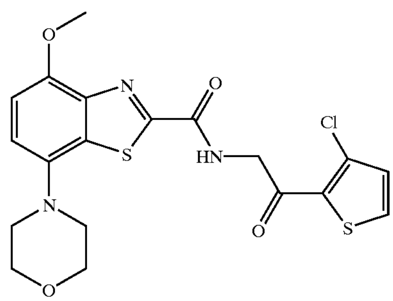 | 4-Methoxy-7-morpholin-4-yl-benzothiazole-2-carboxylic acid [2-(3-chloro-thiophen-2-yl)-2-oxo-ethyl]-amide | 125–127 | 2-(3-Chloro-thien-2-yl)-2-oxo-1-ethanamine |
| 74 | 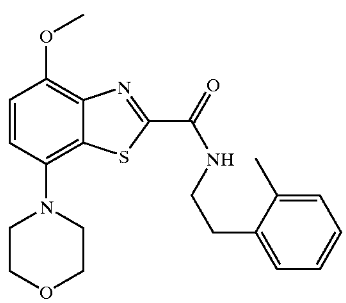 | 4-Methoxy-7-morpholin-4-yl-benzothiazole-2-carboxylic acid (2-o-tolyl-ethyl)-amide | 129–131 | 2-Methyl-phenethyl-amine |
| 75 | 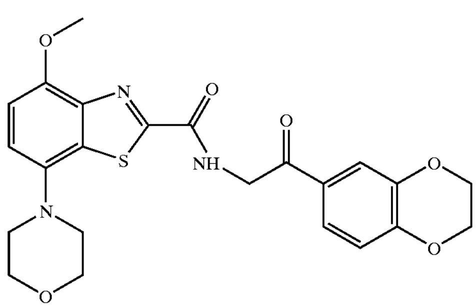 | 4-Methoxy-7-morpholin-4-yl benzothiazole-2-carboxylic acid [2-(2,3-dihydro-benzo[1,4]dioxin-6-yl)-2-oxo-ethyl]-amide | 206–208 | 2-Amino-1-(2,3-dihydro-benzo[1,4]-dioxin-6-yl)-ethanone |

| Exp. No. | Structure | Systematic name | m.p. °C. | adduct |
|---|---|---|---|---|
| 76 | 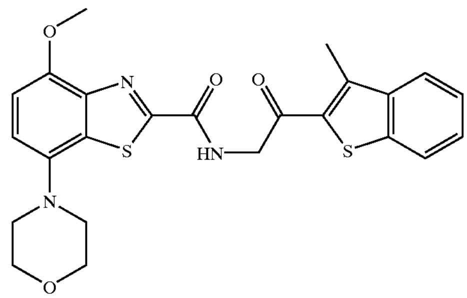 | 4-Methoxy-7-morpholin-4-yl-benzothiazole-2-carboxylic acid [2-(3-methyl-benzo[b]thiophen-2-yl)-2-oxo-ethyl]-amide | 185–187 | 2-Amino-1-(3-methyl-benzo[b]-thiophen-2-yl)-ethanone |
| 77 | 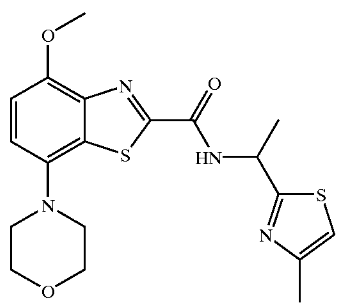 | 4-Methoxy-7-morpholin-4-yl-benzothiazole-2-carboxylic acid [1-(4-methyl-thiazol-2-yl)-ethyl]-amide | 175–176 | alpha-Methyl-2-(4-methyl-thiazole)-methan-amine |
| 78 | 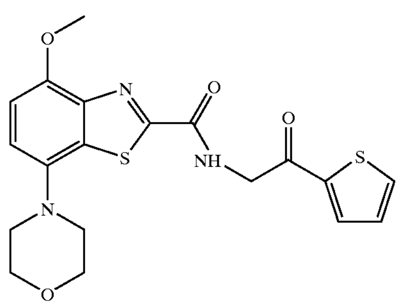 | 4-Methoxy-7-morpholin-4-yl-benzothiazole-2-carboxylic acid (2-oxo-2-thiophen-2-yl-ethyl)-amide | 171–173 | 2-Amino-1-(2-thienyl) ethanone |
| 79 | 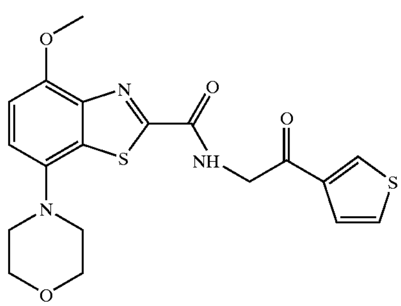 | 4-Methoxy-7-morpholin-4-yl-benzothiazole-2-carboxylic acid (2-oxo-2-thiophen-3-yl-ethyl)-amide | 229–232 | 2-Amino-1-(3-thienyl) ethanone |
| 80 | 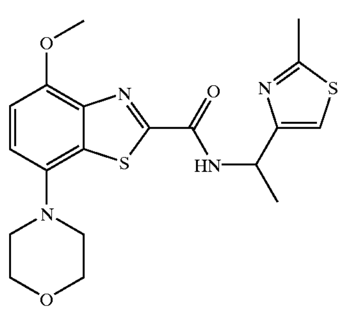 | 4-Methoxy-7-morpholin-4-yl-benzothiazole-2-carboxylic acid [1-(2-methyl-thiazol-4-yl)-ethyl]-amide | 174–175 | 4-(1-Amino-ethyl)-2-methyl-thiazole |

-continued

| Exp. No. | Structure | Systematic name | m.p. ° C. | adduct |
|---|---|---|---|---|
| 81 | 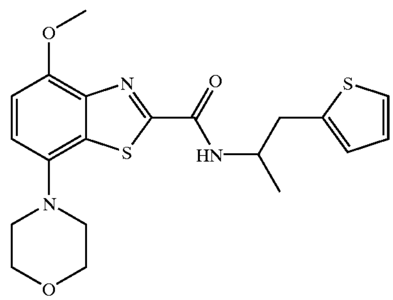 | 4-Methoxy-7-morpholin-4-yl-benzothiazole-2-carboxylic acid (1-methyl-2-thiophen-2-yl-ethyl)-amide | 127–129 | 2-(2-Amino-propyl)-thiophene |
| 82 | 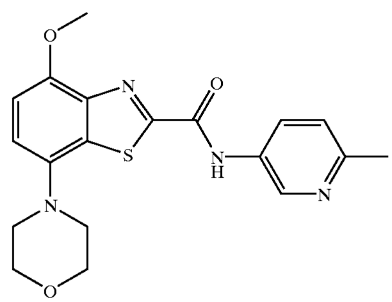 | 4-Methoxy-7-morpholin-4-yl-benzothiazole-2-carboxylic acid (6-methyl-pyridin-3-yl)-amide | 145–147 | 5-Amino-2-methylpyridine |
| 83 | 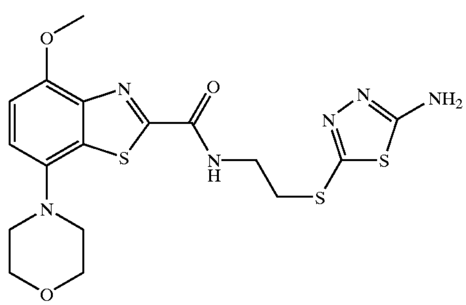 | 4-Methoxy-7-morpholin-4-yl-benzothiazole-2-carboxylic acid [2-(5-amino-[1,3,4]thiadiazol-2-ylsulfanyl)-ethyl]-amide | 237–239 | 2Amino-5-[(2-amino-ethyl)thio]-1,3,4-thiadiazole |
| 84 | 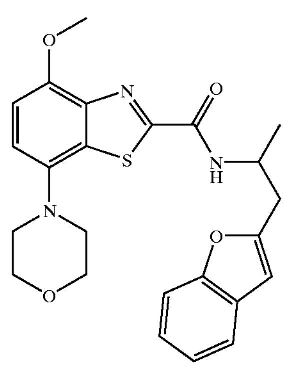 | 4-Methoxy-7-morpholin-4-yl-benzothiazole-2-carboxylic acid (2-benzofuran-2-yl-1-methyl-ethyl)-amide | 144–146 | 2-(2-Amino-propyl)-benzofuran |

What is claimed is:
1. A compound of the formula

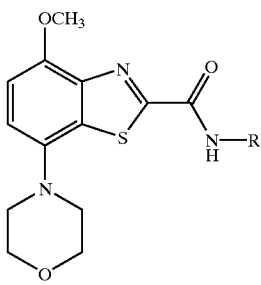

wherein
R is selected from the group
  hydrogen,
  —(CH$_2$)$_n$-phenyl, said —(CH$_2$)$_n$-phenyl being unsubstituted or substituted by a substituent selected from the group halogen, lower alkyl, lower alkoxy, trifluoromethyl and —N(R')—C(O)-lower alkyl,
  —(CH$_2$)$_n$-pyridinyl, said —(CH$_2$)$_n$-pyridinyl being unsubstituted or substituted by lower alkyl,
  —(CH$_2$)$_n$—C$_{3-6}$-cycloalkyl, said —(CH$_2$)$_n$—C$_{3-6}$-cycloalkyl cycloalkyl being unsubstituted or substituted by hydroxy,
  —(CH$_2$)$_n$—N(R')—C$_{3-6}$-cycloalkyl, said —(CH$_2$)$_n$—N(R')—C$_{3-6}$-cycloalkyl being unsubstituted or substituted by hydroxy,
  —(CH$_2$)$_n$-benzo[1,3]-dioxolyl,
  —(CR'$_2$)$_n$-thiophenyl, said —(CR'$_2$)$_n$-thiophenyl being unsubstituted or substituted by lower alkyl,
  —(CR'$_2$)$_n$-thiazolyl, said —(CR'$_2$)$_n$-thiazolyl being unsubstituted or substituted by lower alkyl,
  —(CH$_2$)$_n$—C(O)-thiophenyl, said —(CH$_2$)$_n$—C(O)-thiophenyl being unsubstituted or substituted by halogen,
  —(CH$_2$)$_n$-furanyl, said —(CH$_2$)$_n$-furanyl being unsubstituted or substituted by lower alkyl,
  —(CH$_2$)$_n$—C(O)—(CH$_2$)$_n$-thiophenyl,
  —(CHR')$_n$-benzofuran-2-yl,
  —(CH$_2$)$_n$-benzo[b]thiophenyl, said —(CH$_2$)$_n$-benzo[b]thiophenyl being unsubstituted or substituted by lower alkyl,
  —(CH$_2$)$_n$—N(R')—C(O)-phenyl, said —(CH$_2$)$_n$—N(R')—C(O)-phenyl being unsubstituted or substituted by halogen or lower alkoxy,
  —(CH$_2$)$_n$—C(O)-phenyl, said —(CH$_2$)—C(O)-phenyl being unsubstituted or substituted by lower alkoxy,
  —(CH$_2$)$_n$—C(O)-2,3-dihydro-benzo[1,4]dioxin-6-yl,
  —(CH$_2$)$_n$—N(R')—C(O)-pyridinyl,
  —(CH$_2$)$_n$-tetrahydrofuranyl,
  —CH-bi-phenyl,
  —CH(phenyl)-pyridinyl,
  —(CH$_2$)$_n$-1-oxo-1,3-dihydro-isoindol-2-yl,
  —(CH$_2$)$_n$-1,3-dioxo-1,3-dihydro-isoindol-2-yl,
  —(CH$_2$)$_n$—CH(phenyl)-tetrahydropyranyl,
  —(CH2)$_n$-1-oxo-1,2,3,4-tetrahydro-isoquinolin-3-yl or
  —(CH$_2$)$_n$—S-[1,3,4]thiazol-2-yl, said —(CH$_2$)$_n$—S-[1,3,4]thiazol-2-yl being unsubstituted or substituted by amino;

R' is independently selected from hydrogen and lower alkyl; and n is 0, 1, 2, 3 or 4;
or a pharmaceutically acceptable acid addition salt thereof.

2. The compound of formula I in accordance with claim 1, wherein R is hydrogen.

3. The compound of formula I in accordance with claim 2, wherein the compound is 4-methoxy-7-morpholin-4-yl-benzothiazole-2-carboxylic acid amide.

4. The compound of formula I in accordance with claim 1, wherein R is —(CH$_2$)$_n$-phenyl, said —(CH$_2$)$_n$-phenyl being unsubstituted or substituted by a substituent selected from the group halogen, lower alkoxy and lower alkyl.

5. A compound of formula I in accordance with claim 4, wherein the compound is selected from the group
  4-methoxy-7-morpholin-4-yl-benzothiazole-2-carboxylic acid phenethyl-amide,
  4-methoxy-7-morpholin-4-yl-benzothiazole-2-carboxylic acid 3-chloro-benzylamide,
  4-methoxy-7-morpholin-4-yl-benzothiazole-2-carboxylic acid 2-chloro-benzylamide,
  4-methoxy-7-morpholin-4-yl-benzothiazole-2-carboxylic acid 2-methoxy-benzylamide,
  4-methoxy-7-morpholin-4-yl-benzothiazole-2-carboxylic acid[2-(2-methoxy-phenyl)-ethyl]-amide,
  4-methoxy-7-morpholin-4-yl-benzothiazole-2-carboxylic acid[2-(3-fluoro-phenyl)-ethyl]-amide,
  4-methoxy-7-morpholin-4-yl-benzothiazole-2-carboxylic acid[2-(4-fluoro-phenyl)-ethyl]-amide,
  4-methoxy-7-morpholin-4-yl-benzothiazole-2-carboxylic acid[2-(4-chloro-phenyl)-ethyl]-amide,
  4-methoxy-7-morpholin-4-yl-benzothiazole-2-carboxylic acid[2-(2-chloro-phenyl)-ethyl]-amide,
  4-methoxy-7-morpholin-4-yl-benzothiaizole-2-carboxylic acid[2-(3-methoxy-phenyl)-ethyl]-amide,
  4-methoxy-7-morpholin-4-yl-benzothiazole-2-carboxylic acid[2-(3-chloro-phenyl)-ethyl]-amide and
  4-methoxy-7-morpholin-4-yl-benzothiazole-2-carboxylic acid (2-m-tolyl-ethyl)-amide.

6. The compound of formula I in accordance with claim 1, wherein R is —(CH$_2$)$_n$-pyridinyl said —(CH$_2$)$_n$-pyridinyl being unsubstituted or substituted by lower alkyl.

7. The compound of formula I in accordance with claim 6, wherein the compound is selected from the group
  4-methoxy-7-morpholin-4-yl-benzothiazole-2-carboxylic acid pyridin-3-ylamide,
  4-methoxy-7-morpholin-4-yl-benzothiazole-2-carboxylic acid (pyridin-2-ylmethyl)-amide and
  4-methoxy-7-morpholin-4-yl-benzothiazole-2-carboxylic acid (2-pyridin-3-yl-ethyl)-amide.

8. The compound of formula I in accordance with claim 1, wherein R is —(CHR')$_n$-thiophenyl or —(CHR')$_n$-thiophenyl substituted by halogen.

9. The compound of formula I in accordance with claim 8, wherein the compound is selected from the group
  4-methoxy-7-morpholin-4-yl-benzothiazole-2-carboxylic acid (2-thiophen-2-yl-ethyl)-amide,
  4-methoxy-7-morpholin-4-yl-benzothiazole-2-carboxylic acid (2-thiophen-3-yl-ethyl)-amide,
  4-methoxy-7-morpholin-4-yl-benzothiazole-2-carboxylic acid[2-(3-chloro-thiophen-2-yl)-2-oxo-ethyl]-amide and
  4- methoxy-7-morpholin-4-yl-benzothiazole-2-carboxylic acid (1-methyl-2-thiophen-2-yl-ethyl)-amide.

10. The compound of formula I in accordance with claim 1, wherein R is —(CHR')$_n$-thiazolyl, or —(CHR')$_n$-thiazolyl substituted by lower alkyl.

11. The compound of formula I in accordance with claim 10, wherein the compound is 4-methoxy-7-morpholin-4-yl-benzothiazole-2-carboxylic acid[1-(4-methyl-thiazol-2-yl)-ethyl]-amide.

12. A process for preparing a compound of formula I according to claim 1 comprising reacting a compound of formula

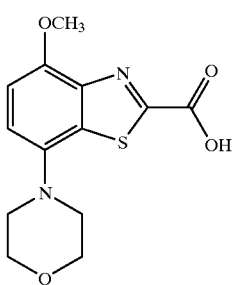
(5)

with a compound of formula

H₂NR (6)

forming a compound of formula

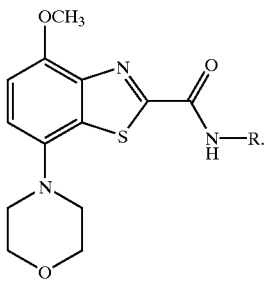
I

13. A process for preparing a compound of formula I according to claim 1 comprising cyclizing a compound of formula

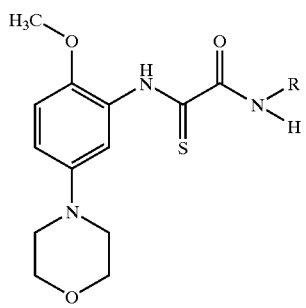
(8)

forming a compound of formula

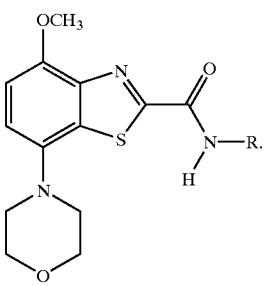
I

14. A pharmaceutical composition comprising a therapeutically effective amount of a compound of formula I according to claim 1, or a pharmaceutically acceptable salt thereof; and a pharmaceutically inert carrier.

15. A method for the treatment of a disease mediated by the adenosine receptor comprising administering a therapeutically effective amount of a compound of formula I, or a pharmaceutically acceptable salt thereof to a person in need of such treatment.

16. A method for the treatment of diseases mediated by the Adenosine $A_{2A}$ receptor comprising administering a therapeutically effective amount of a compound of formula I or a pharmaceutically acceptable salt thereof, to a person in need of such treatment.

* * * * *

UNITED STATES PATENT AND TRADEMARK OFFICE
CERTIFICATE OF CORRECTION

PATENT NO.     : 6,596,718 B1
DATED          : July 22, 2003
INVENTOR(S)    : Flohr et al.

It is certified that error appears in the above-identified patent and that said Letters Patent is hereby corrected as shown below:

<u>Title page,</u>
Item [75], Inventors, "Norcross David Roger" should read
-- Roger David Norcross --.

<u>Column 53,</u>
Line 60, "-(CH2)$_n$-" should read -- -(CH$_2$)$_n$- --.

Signed and Sealed this

Eleventh Day of November, 2003

JAMES E. ROGAN
*Director of the United States Patent and Trademark Office*